(12) United States Patent
Shimizu et al.

(10) Patent No.: US 8,137,986 B2
(45) Date of Patent: Mar. 20, 2012

(54) NON-LIQUID PHASE TYPE CHEMILUMINESCENT ENZYME IMMUNOASSAY METHOD AND ASSAY KIT

(75) Inventors: Koichi Shimizu, Sapporo (JP); Takeshi Kawaguchi, Tokyo (JP); Yasuyo Maeda, Tokyo (JP); Takehide Matsuda, Tokyo (JP)

(73) Assignees: National University Corporation Hokkaido University, Sapporo-shi, Hokkaido (JP); Seiken Co., Ltd., Tokyo (JP); Aska Special Laboratory Co., Ltd., Kawasaki-shi, Kanagawa (JP)

( * ) Notice: Subject to any disclaimer, the term of this patent is extended or adjusted under 35 U.S.C. 154(b) by 725 days.

(21) Appl. No.: 12/084,254

(22) PCT Filed: Oct. 30, 2006

(86) PCT No.: PCT/JP2006/321675
§ 371 (c)(1),
(2), (4) Date: Apr. 29, 2008

(87) PCT Pub. No.: WO2007/052613
PCT Pub. Date: May 10, 2007

(65) Prior Publication Data
US 2009/0142781 A1 Jun. 4, 2009

(30) Foreign Application Priority Data
Oct. 31, 2005 (JP) ................................ 2005-342785

(51) Int. Cl.
*G01N 331/543* (2006.01)
(52) U.S. Cl. ....................................................... 436/518
(58) Field of Classification Search .................. None
See application file for complete search history.

(56) References Cited

U.S. PATENT DOCUMENTS 6,306,642 B1 * 10/2001 Nelson et al. ............. 435/287.1
2004/0096991 A1 * 5/2004 Zhang ......................... 436/518

FOREIGN PATENT DOCUMENTS

| EP | 0200507 A1 | 11/1986 |
|----|----|----|
| EP | 0225054 A1 | 6/1987 |
| JP | 61247965 A | 11/1986 |
| JP | 2038971 A | 2/1990 |
| JP | 3-53897 A | 3/1991 |
| JP | 3503928 A | 8/1991 |
| JP | 4303769 A | 10/1992 |
| JP | 10185921 A | 7/1998 |
| JP | 2001-249079 A | 9/2001 |
| JP | 3481894 B2 | 12/2003 |
| WO | 03/014740 A1 | 2/2003 |
| WO | 2005/001427 A2 | 1/2005 |
| WO | 2007/052613 A1 | 5/2007 |

OTHER PUBLICATIONS

European Search Report in counterpart application No. 06 812 184. 7-2404, mailed Oct. 22, 2010.
English Abstract for Japanese Patent Application No. 2005-61910 A; online:: http://www19.ipdl.inpit.go.jp/PA1/cgi-bin/PA1DETAIL, one page, downloaded on Jan. 26, 2012.

* cited by examiner

*Primary Examiner* — Ann Lam
(74) *Attorney, Agent, or Firm* — The Nath Law Group; Joshua B. Goldberg; Tanya E. Harkins

(57) ABSTRACT

A chemiluminescent enzyme immunoassay method whereby a target substance such as a protein is assayed. This chemiluminescent enzyme immunoassay method comprises: the step of capturing an immune complex containing an enzyme-labeled antibody, which is labeled with an enzyme acting a chemiluminescent substrate, and the target substance on a support having no solution layer; the step of overlaying a support membrane containing the chemiluminescent substrate on the immune complex having been captured above; and the step of measuring the luminescence dose caused by the reaction between the enzyme-labeled antibody and the chemiluminescent substrate to thereby quantify the target substance. Since a highly sensitive chemiluminescent enzyme immunoassay is conducted by using a non-liquid phase type reaction system in the chemiluminescent enzyme immunoassay method as described above, multiple items can be assayed by using only a small amount of a specimen and, furthermore, the target substance can be assayed at a high sensitivity thereby without resorting to any troublesome procedures such as pipetting a reagent.

14 Claims, 6 Drawing Sheets

NON-LIQUID PHASE TYPE CHEMILUMINESCENT ENZYME IMMUNOASSAY METHOD AND ASSAY KIT

FIELD OF THE INVENTION

The present invention relates to a chemiluminescent enzyme immunoassay method and an assay kit, particularly, a non-liquid phase type chemiluminescent enzyme immunoassay method measuring biogenic substances such as proteins and an assay kit using thereof.

BACKGROUND ART

Immunoassay is a measuring method which utilizes the characteristics of specifically binding antibody to the target substance as antigen. As a representative immunoassay, enzyme immunoassay (EIA) is generally known. The measurement sensitivity in EIA is high to be in a few ng/mL level, and EIA is widely used as a method of testing carcinoma-associated proteins, viruses and the like, in a study, a clinical examination and the like. Further, recently, more highly sensitive assays receive much attention, because of an item requiring a measurement sensitivity of 1 ng/mL or less, a small amount of test samples to use, and the like, so that chemiluminescent enzyme immunoassay (CLEIA) method has started to become popular (for example, see Patent Documents 1 and 2).

In conventional enzyme immunoassay and chemiluminescent enzyme immunoassay, a method is adopted in which a specific antibody selectively binding to the target substance such as protein is immobilized to a vessel such as a test tube or a 96-well plastic microplate; plastic beads; or magnetostrictive material such as ferrite, and the target substance is selectively taken out from a liquid layer. Such a method in which a reaction is carried out in a test tube, microplate or the like, and the color tone or fluorescent substance or luminescent substance appeared in a liquid layer is measured, is referred to as liquid-phase type assay method, and has problems that the assay procedures such as injection of reagents and drainage are troublesome and that the assay equipment is large.

On the other hand, non-liquid phase type immunoassay methods are also developed, and as a representative, there is an immunochromatography method. Immunochromatography is the method of measuring the target substance by intensively capturing an immune complex of the target substance and labeled antibody (labeled with a visualizing substance such as gold colloid particle and color latex) in a section linearly arranged with antibodies on a test device, and visually or optically reading the captured immune complex (appeared as a colored line) (for example, see Patent Document 3). In the immunochromatography method, approximate concentration of the target substance is obtained only by observing the appeared line after applying a sample such as urine and blood into a sample applying section, and thus the operation is easy. The sample volume required for the immunochromatography method is about 100 μL, but the sensitivity for the measurement is about 1 ng/mL.

Patent Document 1: Japanese Patent Laid-Open Publication No. H03-53897
Patent Document 2: Japanese Patent Laid-Open Publication No. 2001-249079
Patent Document 3: Japanese Patent No. 3481894

SUMMARY OF THE INVENTION

Problem to be Solved by the Invention

As described above, a chemiluminescent enzyme immunoassay method has a significantly high sensitivity, and is used for the assay of a trace amount of proteins and the like. However, a chemiluminescent enzyme immunoassay method conventionally used has a problem that when adapted to an autoanalyzer, the autoanalyzer becomes large in size and expensive in cost. That is, a chemiluminescent enzyme immunoassay method conventionally used is a liquid-phase type assay method, and requires a troublesome mechanism such as a dispensing mechanism for sample and reagent as well as a washing mechanism for B/F separation when adapted to an autoanalyzer. As a result, the autoanalyzer to which a chemiluminescent enzyme immunoassay method conventionally used is adapted becomes large in size and expensive in cost.

Therefore, the present inventors examined the development an immunoassay having both characteristics of liquid-phase type chemiluminescent enzyme immunoassay method (for example, less influenced by external light, and having high sensitivity) and characteristics of non-liquid phase type immunochromatography method (for example, the washing step for B/F separation is unnecessary).

Means for Solving the Problems

The present inventors examined application of the principle of chemiluminescence to a non-liquid phase type immunochromatography method. Chemiluminescence is a phenomenon of emitting light as energy when the molecule excited by enzymatic catalysis returns to a stable state. In a measuring method using chemiluminescence, generally an enzyme, a chemiluminescent substrate and a chemiluminescent enhancer are mixed in a solution to emit light from the whole solution, and the amount of the emitted light is measured. The chemiluminescent enzyme immunoassay method described in Patent Documents 1 and 2 and the like is an immunoassay using this liquid phase type chemiluminescent reaction system.

The present inventors examined the development of a non-liquid phase type chemiluminescent enzyme immunoassay method by using an enzyme acting on a chemiluminescent substrate but not on visible gold colloid as the labeling substance for an antibody in immunochromatography. As a result of the study, it was found that, to measure by chemiluminescence the immune complex (containing an enzyme-labeled antibody) captured on a test device, even when a solution of chemiluminescent substrate or a solution of chemiluminescent enhancer is applied on the test device, the produced light-emitting product diffuses without being immobilized on the periphery of the immune complex so that a stable subject to be measured is no obtained.

The present inventors found that a light-emitting product is obtained stably on a support membrane not by applying directly the solution of a chemiluminescent substrate on a test device but by overlaying the support membrane containing the chemiluminescent substrate on a test device, and accomplished the present invention.

Furthermore, the present inventors found that the light-emitting product may be obtained stably on the support membrane even in a reaction system that requires a chemiluminescent enhancer similarly to the case of no chemiluminescent enhancer, by overlaying the support membrane containing a chemiluminescent enhancer on a test device and furthermore overlaying the support membrane containing a chemiluminescent substrate on the support membrane containing the chemiluminescent enhancer, and accomplished the present invention.

That is, the first aspect of the present invention relates to the chemiluminescent enzyme immunoassay method described below.

(1) A non-liquid phase type chemiluminescent enzyme immunoassay method, comprising the step of capturing an immune complex containing an enzyme-labeled antibody labeled with an enzyme acting on a chemiluminescent substrate, and a target substance on a support base; the step of overlaying a support membrane containing the chemiluminescent substrate on the immune complex; and the step of measuring an amount of the target substance by detecting an amount of luminescence generated by a reaction between the enzyme-labeled antibody and the chemiluminescent substrate.

(2) The non-liquid phase type chemiluminescent enzyme immunoassay method according to (1), wherein the support membrane is transparent or semitransparent.

(3) The non-liquid phase type chemiluminescent enzyme immunoassay method according to (2), wherein the support membrane is agarose gel, polyacrylamide gel or cellulose acetate membrane.

(4) The non-liquid phase type chemiluminescent enzyme immunoassay method according to (1) to (3), wherein the support membrane further contains a chemiluminescent enhancer.

(5) The non-liquid phase type chemiluminescent enzyme immunoassay method according to (1) to (3), further comprising the step of overlaying a support membrane containing a chemiluminescent enhancer on the immune complex.

(6) The non-liquid phase type chemiluminescent enzyme immunoassay method according to (5), wherein the support membrane containing the chemiluminescent enhancer is placed between the immune complex and the support membrane containing the chemiluminescent substrate.

(7) The non-liquid phase type chemiluminescent enzyme immunoassay method according to (1) to (6), wherein the target substance contains a protein or a chemical.

(8) The non-liquid phase type chemiluminescent enzyme immunoassay method according to (1) to (7), wherein the step of measuring includes the step of quantifying the concentration of the target substance from the detected luminescence amount and a previously prepared calibration curve.

The second aspect of the present invention relates to an assay kit described below.

(9) An assay kit using a non-liquid phase type chemiluminescent enzyme immunoassay method, comprising a test device having a sample-applying section to be applied with a sample containing a target substance, a labeled-antibody holding section containing an enzyme-labeled antibody labeled with an enzyme acting on a chemiluminescent substrate, a measuring section capturing an immune complex containing the target substance and the enzyme-labeled antibody, and a support base to be placed with the sample-applying section, the labeled-antibody holding section and the measuring section; and a support membrane containing the chemiluminescent substrate.

(10) The assay kit according to (9), wherein the test device further has a second measuring section capturing the antibody or the immune complex on the support base.

(11) The assay kit according to (9) or (10), wherein the support membrane is agarose gel, polyacrylamide gel or cellulose acetate membrane.

(12) The assay kit according to (9) to (11), wherein the support membrane further contains a chemiluminescent enhancer.

(13) The assay kit according to (9) to (12), wherein the kit further has a support membrane containing a chemiluminescent enhancer.

Effect of the Invention

According to the present invention, as a non-liquid phase type chemiluminescent enzyme immunoassay method is used, the target substance can be measured in high sensitivity without any troublesome procedures including dispensing reagents, washing and stirring. Furthermore, according to the present invention, as the above-described troublesome procedures are not necessary, measuring equipments with small in size and low in cost can be produced.

BEST MODE FOR CARRYING OUT THE INVENTION

A non-liquid phase type chemiluminescent enzyme immunoassay method of the present invention is characterized in that, using an antibody labeled with an enzyme catalyzing a chemiluminescent substrate, and carrying out a reaction between an enzyme-labeled antibody and a chemiluminescent substrate on a support membrane. Thus, the reaction product may be kept on the support membrane. In the present specification, the reaction system generating chemiluminescence by reacting a reagent solution in a reaction vessel is referred to as "liquid phase type reaction system", and conventionally-used chemiluminescent enzyme immunoassay method using liquid phase type reaction system is referred to as "a liquid phase type chemiluminescent enzyme immunoassay method". Furthermore, the present inventors defined the reaction system in which the support membrane containing a chemiluminescent substrate is overlaid on an enzyme-labeled antibody on a support base to generate chemiluminescence on the support membrane without a solution layer, as "non-liquid phase type reaction system", and a chemiluminescent enzyme immunoassay method of the present invention using a non-liquid phase type reaction system as "a non-liquid phase type chemiluminescent enzyme immunoassay method". In the chemiluminescent enzyme immuno assay method of the present invention (i.e. non-liquid phase type chemiluminescent enzyme immunoassay method), chemiluminescence may be generated without using a vessel such as a test tube and a microplate, and may be kept stably.

In the chemiluminescent enzyme immunoassay method of the present invention, target substances such as proteins and chemicals are measured with the use of non-liquid phase type reaction system. The term "Measuring" in the present specification includes not only measuring the concentration (amount) of a target substance but also detecting the presence or the absence of a target substance.

In the chemiluminescent enzyme immunoassay method of the present invention, since the reaction product may be kept on a support membrane without spreading onto a support base, the target substance may be measured stably. Furthermore, in the chemiluminescent enzyme immunoassay method of the present invention, since a washing step as in a liquid-phase type chemiluminescent enzyme immunoassay method is not necessary, procedures of exchanging a solution such as a buffer solution can be excluded and a simple procedure is enough to be employed.

Hereafter, the embodiments of the present invention are illustrated with reference to the Drawings.

The First Embodiment

Figure 1:
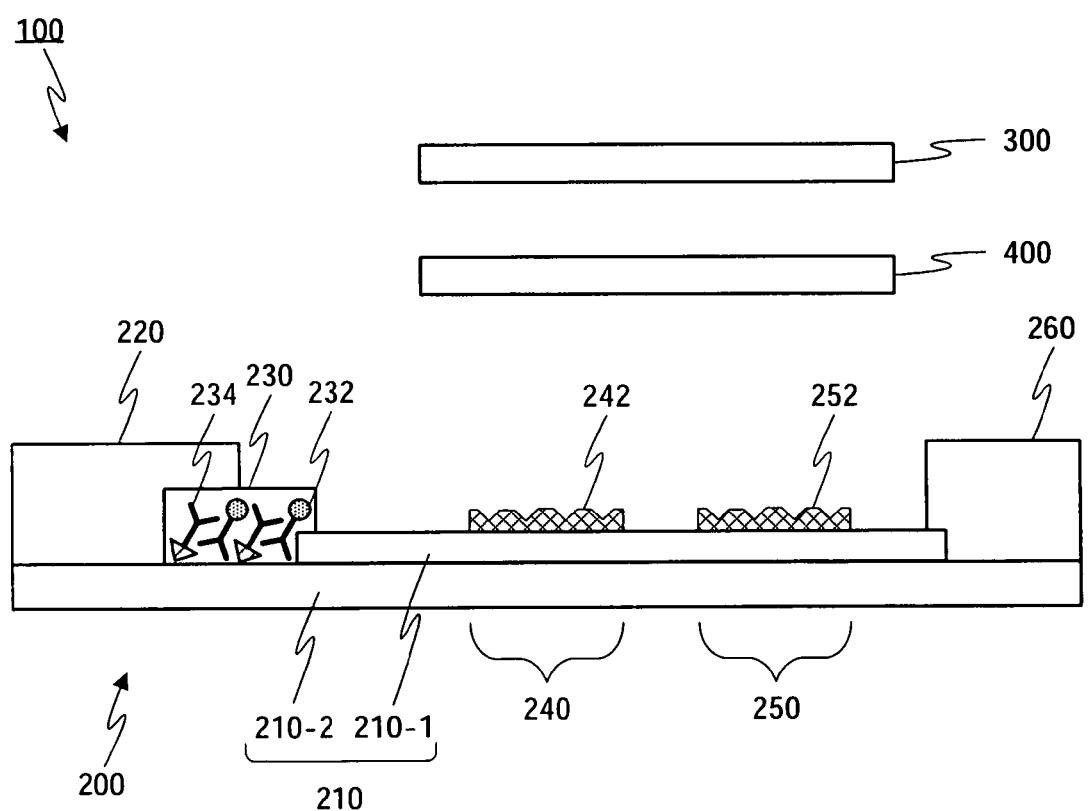
FIG. 1 is a schematic view showing the construction of the assay kit according to the first embodiment of the present invention.

FIG. 1 is a view showing the construction of the assay kit according to the first embodiment of the present invention.

In FIG. 1, an assay kit 100 has a test device 200, a support membrane for chemiluminescent substrate 300 and a support membrane for chemiluminescent enhancer 400.

A test device 200 has a support base 210, a sample applying section 220, a labeled-antibody holding section 230, a first measuring section 240, a second measuring section 250 and an absorption section 260. The sample applying section 220, the labeled-antibody holding section 230, the first measuring section 240, the second measuring section 250 and the absorption section 260 are formed on the support base 210, and are preferred to be placed in this order.

The support base 210 contains a membrane 210-1 to develop a subject sample by capillary phenomenon, and as an example of the membrane 210-1, a nitrocellulose membrane or a nylon membrane may be mentioned. The support base 210 is preferred to further have a support plate 210-2 on which the membrane 210-1 is attached to ensure the strength. As examples of the support plate 210-2, a glass plate, a synthetic resin plate or the like may be mentioned. There is no need to have a solution layer in the support base 210. Thus, a vessel is not required to be formed in the support base.

The sample applying section 220 is a section to be applied with a subject sample, and is constructed by, for example, nonwoven fabric made from rayon, filter paper, cotton cloth (absorbent cotton) and the like. The sample applying section 220 is preferred to be in contact with the labeled-antibody holding section 230.

The labeled-antibody holding section 230 is a member containing in a movable state an enzyme-labeled antibody 232 and an antibody labeled with a substance binding to the first measuring section 240 and the second measuring section 250 (hereafter referred to as "an antibody labeled with a substance binding to a measuring section"), and is, for example, nonwoven fabric made from glass fiber and the like. The enzyme-labeled antibody 232 and the antibody labeled with a substance binding to a measuring section 234 which are contained in the labeled-antibody holding section 230 are preferred to be dry for ease of storing a test device.

The enzyme-labeled antibody 232 is an antibody binding to a target substance, labeled with an enzyme catalyzing a chemiluminescent reaction. The enzyme-labeled antibody 232 may be a primary antibody directly binding to the target substance, or may be a secondary or tertiary antibody binding to the target substance via the other antibody.

An enzyme which labels the enzyme-labeled antibody 232 may be appropriately selected depending on the chemiluminescent substrate contained in a chemiluminescent substrate supporting membrane 300, for example alkaline phosphatase thereafter abbreviated as "ALP"), luciferase, horseradish peroxidase (hereafter abbreviated as "HRP") and the like.

The antibody labeled with a substance binding to a measuring section 234 is an antibody binding to a target substance, labeled with a substance which binds to the first measuring section 240 and the second measuring section 250. For example, when avidin or streptavidin which is a biotin-specific binding protein is immobilized in the first measuring section 240 and the second measuring section 250, the antibody labeled with a substance binding to a measuring section 234 is an antibody binding to the target substance, labeled with biotin.

In the labeled-antibody holding section 230, the target substance contained in the subject sample moved from the sample applying section 220, the enzyme-labeled antibody 232 and the antibody labeled with a substance binding to a measuring section 234 bind together to form an immune complex.

The first measuring section 240 is a band-shaped or dot-shaped section capturing the immune complex formed in the labeled-antibody holding section 230. In the first measuring section 240, a substance 242 which binds to the antibody labeled with a substance binding to a measuring section 234 is preferably immobilized. For example, when the antibody labeled with a substance binding to a measuring section is an antibody labeled with biotin, avidin or streptavidin is preferably immobilized in the first measuring section 240. The first measuring section 240 binds to the antibody labeled with a substance binding to a measuring section 234 bound to the target substance, and captures the immune complex.

The second measuring section 250 is a band-shaped or dot-shaped section capturing the immune complex that was not captured in the first measuring section 240. In the second measuring section 250, the substance 252 is immobilized which binds to the antibody labeled with a substance binding to a measuring section like the first measuring section 240. The second measuring section 250 binds to the antibody labeled with a substance binding to a measuring section 234 bound to the target substance, and captures an immune complex.

Absorption section 260 is a section absorbing liquid (usually water) contained in the subject sample, and is constructed of, for example, a filter paper and the like.

A support membrane for chemiluminescent substrate 300 is a dry-type or wet-type support membrane containing a chemiluminescent substrate. The support membrane for chemiluminescent substrate 300 is preferably transparent or semi-transparent from the viewpoint of measuring the luminescence from the reaction between an enzyme which labels an enzyme-labeled antibody 232 and a chemiluminescent substrate, and is for example, agarose gel, polyacrylamide gel, cellulose acetate membrane and the like. When gel such as agarose gel and polyacrylamide gel is used, these gels are preferably immobilized on a transparent polyester film, polyethylene film or the like for supporting gel. For example, there are Gel Bond Film (Cambrex Corporation) for agarose gel and Gel Bond PAG Film (Cambrex Corporation) for polyacrylamide gel, and the like.

A chemiluminescent substrate contained in the support membrane for chemiluminescent substrate 300 may be appropriately selected depending on an enzyme which labels an enzyme-labeled antibody 232. For example, when the enzyme which labels an enzyme-labeled antibody 232 is ALP, a dioxetane-based compound such as CDP-Star and CSPD (Roche Diagnostics), and the like may be selected as a chemiluminescent substrate. Furthermore, when the enzyme which labels an enzyme-labeled antibody 232 is luciferase, luciferin (Dojindo Laboratories, and others) and the like may be selected as a chemiluminescent substrate. Furthermore, when the enzyme which labels an enzyme-labeled antibody 232 is HRP, luminol (Pierce, Co., and others) and the like may be selected as a chemiluminescent substrate.

To add a chemiluminescent substrate in the support membrane for chemiluminescent substrate 300, for example, in the case of agarose gel, polyacrylamide gel and the like, a chemiluminescent substrate is added to a composition for producing a gel, and then the composition may be solidified or polymerized. Furthermore, in the case of a cellulose acetate membrane, a chemiluminescent substrate is immersed into a cellulose acetate membrane, and then the unnecessary chemiluminescent substrate may be removed.

A support membrane for chemiluminescent enhancer 400 is a dry-type or wet-type support membrane containing a chemiluminescent enhancer. The support membrane for chemiluminescent enhancer 400 is, for example, agarose gel, polyacrylamide gel, cellulose acetate membrane, filter paper, and the like.

The chemiluminescent enhancer contained in the support membrane for chemiluminescent enhancer 400 may be appropriately selected depending on the reaction system of chemiluminescence. For example, when the enzyme which labels an enzyme-labeled antibody 232 is ALP, a water-soluble polymer containing a quaternary ammonium group such as a myristyl trimethyl ammonium bromide, a cetyl trimethyl ammonium bromide, a poly[vinyl benzyl (benzyl dimethyl ammonium chloride)], and a polyvinyl benzyl tributyl ammonium chloride, Nitro-Block (Tropix), or the like may be selected as a chemiluminescent enhancer. Furthermore, when the enzyme which labels an enzyme-labeled antibody 232 is luciferase, ATP and the like may be selected as a chemiluminescent enhancer. Furthermore, when the enzyme which labels an enzyme-labeled antibody 232 is HRP, phenol and the like may be selected as a chemiluminescent enhancer.

To add a chemiluminescent enhancer in the support membrane for chemiluminescent substrate 400, for example, in the case of agarose gel, polyacrylamide gel and the like, a chemiluminescent enhancer is added to a composition for producing a gel, and then the composition may be solidified or polymerized. Furthermore, in the case of a cellulose acetate membrane, a filter paper and the like, a chemiluminescent enhancer is immersed into a cellulose acetate membrane or a filter paper, and then the unnecessary chemiluminescent enhancer may be removed.

By the way, there are some cases in which a chemiluminescent enhancer is not required depending on the reaction system of chemiluminescence. In these cases, the support membrane for chemiluminescent enhancer 400 is not required. Furthermore, although a support membrane (a support membrane for chemiluminescent substrate 300) containing a chemiluminescent substrate and a support membrane (a support membrane for chemiluminescent enhancer 400) containing a chemiluminescent enhancer have been described separately, one support membrane may contain a chemiluminescent substrate and a chemiluminescent enhancer. In the latter case, the support membrane containing a chemiluminescent substrate and a chemiluminescent enhancer is, for example, agarose gel, polyacrylamide gel, cellulose acetate membrane, filter paper and the like. The ratio between a chemiluminescent substrate and a chemiluminescent enhancer may be appropriately adjusted to, for example, chemiluminescent substrate:chemiluminescent enhancer=1:10.

Figure 2A:
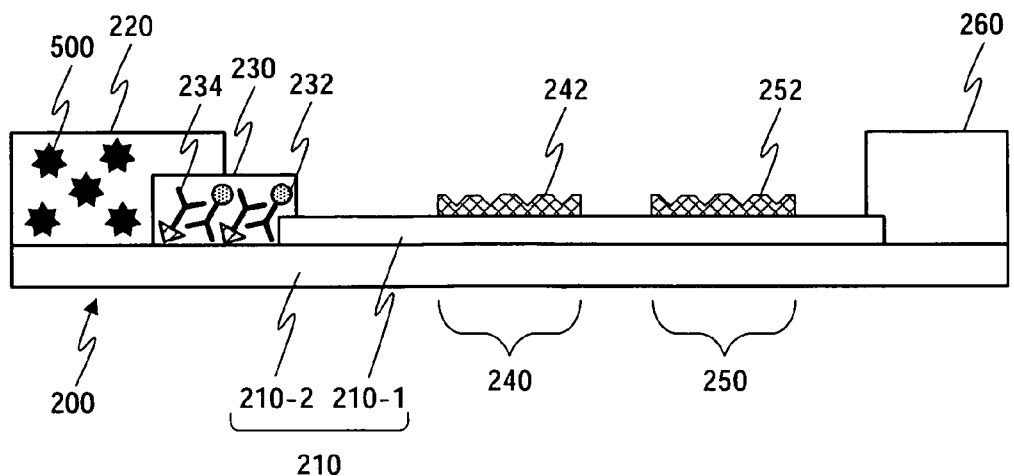
FIG. 2 is a view showing the principle of the non-liquid phase type chemiluminescent enzyme immunoassay method according to the first embodiment of the present invention.

Next, with reference to the schematic view of FIG. 2, the principle of measuring a target substance with the assay kit according to the first embodiment is illustrated. A solvent of the subject sample is not shown in FIG. 2 for convenience of explanation.

When the subject sample containing a target substance 500 is applied into a sample applying section 220 (FIG. 2A), the subject sample passes through a labeled-antibody holding section 230 and a surface of a membrane 210-1 by capillary phenomenon, and moves to a absorption section 260. At this time, in the labeled-antibody holding section 230, the target substance 500 contained in the subject sample, an enzyme-labeled antibody 232 and an antibody labeled with a substance binding to a measuring section 234 bind together to form an immune complex 510.

Figure 2B:
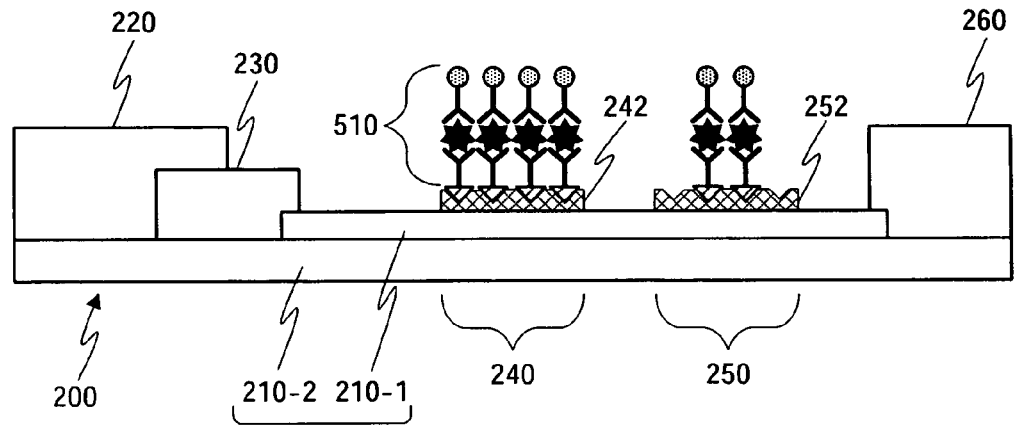

The formed immune complex 510 moves on the surface of the membrane 210-1 toward the absorption section 260. Since the antibody labeled with a substance binding to a measuring section 234 contained in the immune complex 510 binds to the first measuring section 240, most of the immune complex 510 are captured in the first measuring section 240 (FIG. 2B). The remaining immune complex 510 further moves on the surface of the membrane 210-1 toward the absorption section 260, and is captured in the second measuring section 250 (FIG. 2B).

Figure 2C:
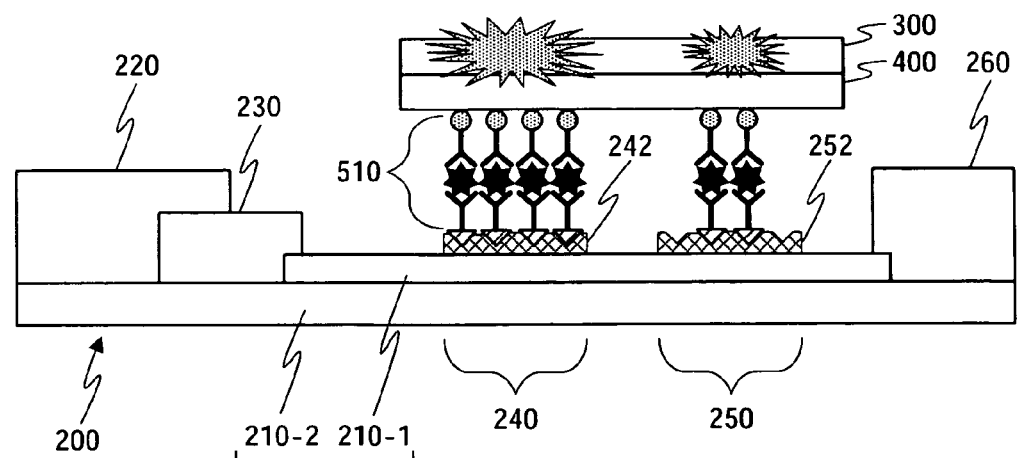

On the first measuring section 240 and the second measuring section 250, a support membrane for chemiluminescent enhancer 400 is overlaid, on which a support membrane for chemiluminescent substrate 300 is further overlaid, resulting in generation of chemiluminescence in the first measuring section 240 and the second measuring section 250, wherein an enzyme that labels an enzyme-labeled antibody 232 acts on the substrate contained in the support membrane for chemiluminescent substrate 300 (FIG. 2C). The chemiluminescence is detected by an optical procedure such as a cooled CCD camera or a photomultiplier to measure the target substance 500 contained in the subject sample. At this time, the state of the reaction system (for example, the presence or absence of prozone phenomenon) may be evaluated by comparing the amount of luminescence in the first measuring section 240 and the amount of luminescence in the second measuring section 250. The concentration (amount) of the target substance 500 in the subject sample may be measured by applying the amount of luminescence in the first measuring section 240 to a previously prepared calibration curve.

As illustrated above, the chemiluminescent enzyme immunoassay method and the assay kit according to the present embodiment provide a chemiluminescent substrate and a chemiluminescent enhancer not in a solution state but in an immersed state in a support membrane on the first measuring section and the second measuring section which have captured the immune complex containing an enzyme-labeled antibody. Thus, the chemiluminescent enzyme immunoassay method and the assay kit according to the present embodiment can realize a high-sensitive chemiluminescent enzyme immunoassay method by using the convenient non-liquid phase type reaction system.

The Second Embodiment

In the first embodiment, an example was shown in which an antibody labeled with a substance binding to a measuring section was bound to a target substance in a labeled-antibody holding section and the immune complex was captured in the first measuring section and the second measuring section. In the second embodiment, an example is shown in which an antibody binding to a target substance is immobilized in advance in the first measuring section and the second measuring section, and the immune complex is captured in the first measuring section and the second measuring section.

Figure 3:
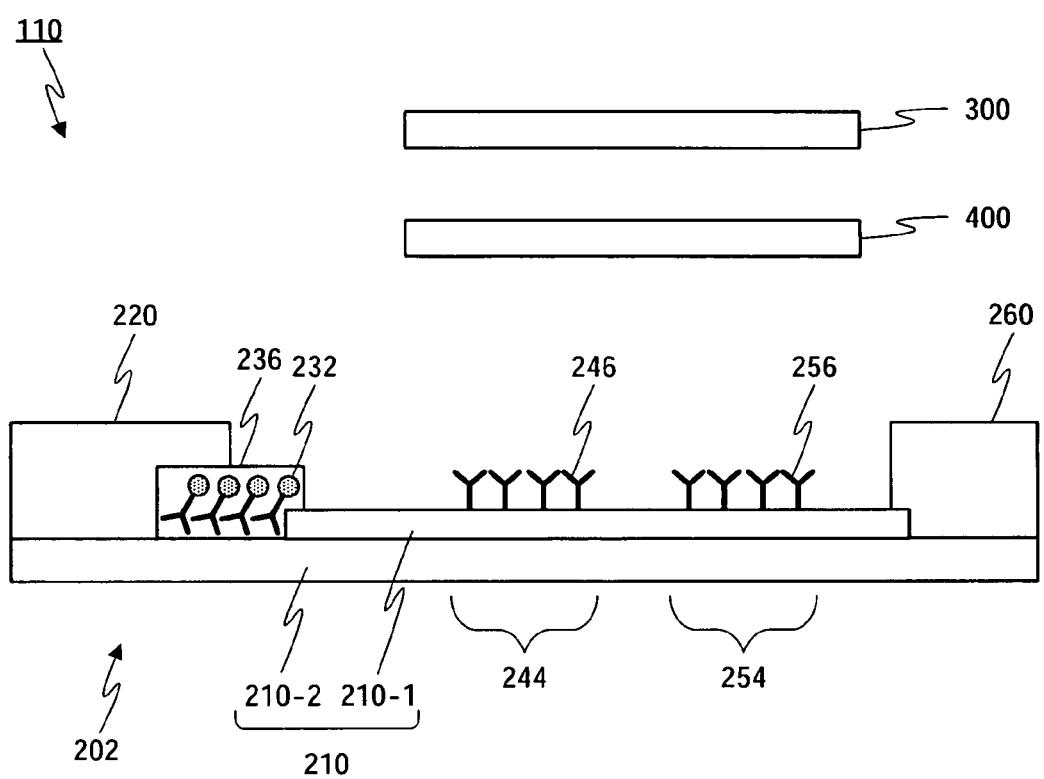
FIG. 3 is a schematic view showing the construction of the assay kit according to the second embodiment of the present invention.

FIG. 3 is a view showing the construction of the assay kit according to the second embodiment of the present invention. The same components as in the assay kit according to the first embodiment are appended with the identical code, and the overlapping explanation is omitted.

In FIG. 3, an assay kit 110 has a test device 202, a support membrane for chemiluminescent substrate 300 and a support membrane for chemiluminescent enhancer 400. The support membrane for chemiluminescent substrate 300 and the support membrane for chemiluminescent enhancer 400 are same as those in the first embodiment.

The test device 202 has a support base 210, a sample applying section 220, a labeled-antibody holding section 236, a first measuring section 244, a second measuring section 254 and an absorption section 260. The support base 210, the sample applying section 220 and the absorption section 260 are same as those in the first embodiment.

The labeled-antibody holding section 236 is a member containing the enzyme-labeled antibody 232 in a movable state. The enzyme-labeled antibody 232 contained in the labeled-antibody holding section 236 is same as the enzyme-labeled antibody according to the first embodiment, and is preferably dry. In the labeled-antibody holding section 236, a target substance contained in a subject sample and the enzyme-labeled antibody 232 bind together to form an immune complex.

The first measuring section 244 is a band-shaped or dot-shaped section which captures the immune complex formed in the labeled-antibody holding section 236, like the first measuring section according to the first embodiment. The capturing antibody 246 binding to the target substance is immobilized in the first measuring section 240. The first measuring section 244 binds to the target substance contained in the immune complex to capture the immune complex.

The second measuring section 254 is a band-shaped or dot-shaped section which captures the immune complex not captured in the first measuring section 244, similarly to the second measuring section according to the first embodiment. In the second measuring section 254, similarly to the first measuring section 244, a capturing antibody 256 binding to the target substance is immobilized and binds to the target substance contained in the immune complex to capture the immune complex.

Figure 4A:
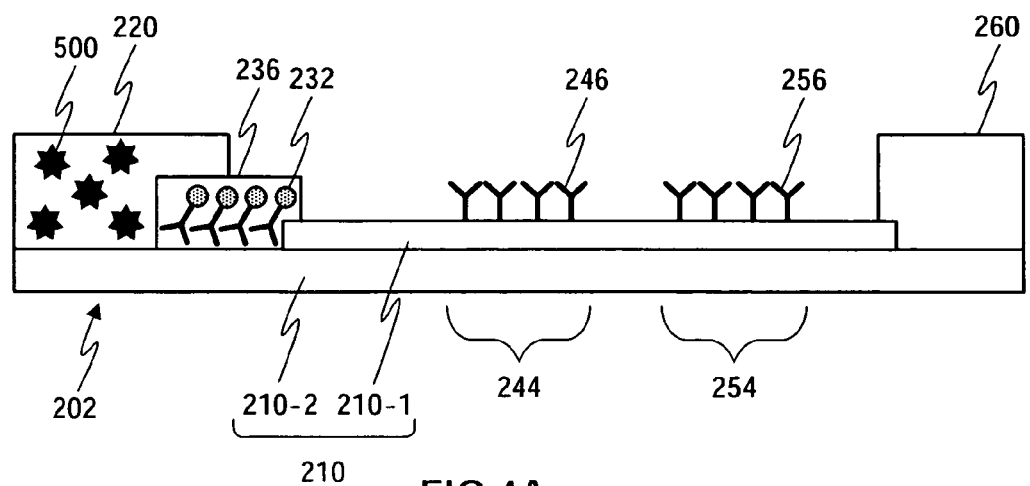
FIG. 4 is a view showing the principle of the non-liquid phase type chemiluminescent enzyme immunoassay method according to the second embodiment of the present invention.

Next, with reference to the schematic view of FIG. 4, the principle of measuring a target substance with the assay kit according to the second embodiment is illustrated. A solvent of the subject sample is not shown in FIG. 4 for convenience of explanation.

When the subject sample containing a target substance 500 is applied into a sample applying section 220 (FIG. 4A), the subject sample passes through the labeled-antibody holding section 236 and a surface of a membrane 210-1 by capillary phenomenon, and moves to an absorption section 260. At this time, the target substance 500 contained in the subject sample and the enzyme-labeled antibody 232 bind together in the labeled-antibody holding section 236 to form an immune complex 510.

Figure 4B:
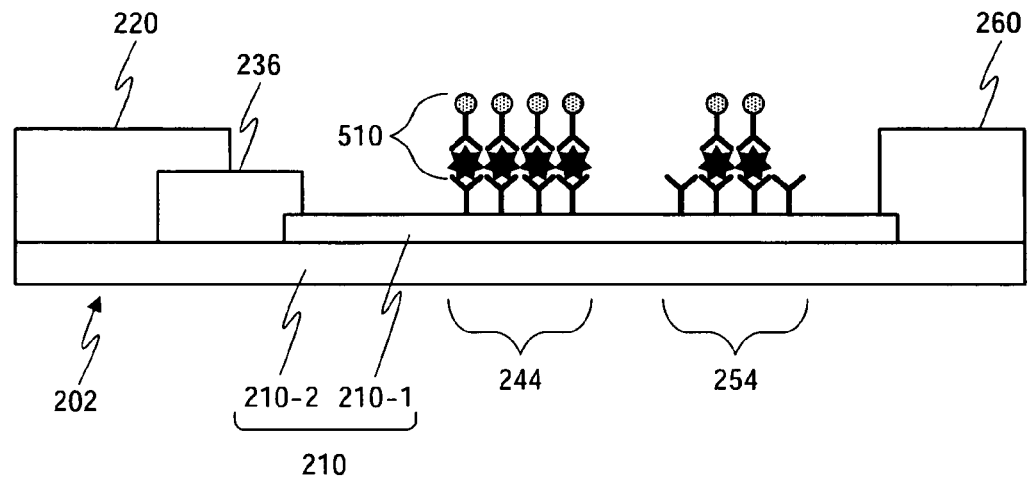

The formed immune complex 510 moves on the surface of the membrane 210-1 toward the absorption section 260. Since the captured antibody 246 immobilized in the first measuring section 244 binds to the immune complex 510, most of the immune complex 510 are captured in the first measuring section 244 (FIG. 4B). The remaining immune complex 510 further moves on the surface of the membrane 210-1 toward the absorption section 260, and is captured in the second measuring section 254 (FIG. 4B).

Figure 4C:
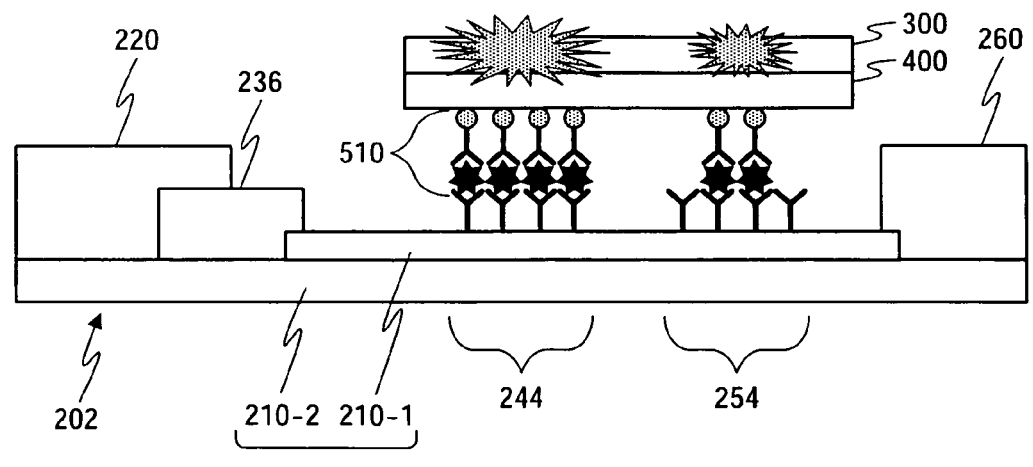

On the first measuring section 244 and the second measuring section 254, a support membrane for chemiluminescent enhancer 400 is overlaid, on which a support membrane for chemiluminescent substrate 300 is further overlaid, resulting in generation of chemiluminescence in the first measuring section 244 and the second measuring section 254, wherein the enzyme that labels an enzyme-labeled antibody 232 acts on the substrate contained in the support membrane for chemiluminescent substrate 300 (FIG. 4C). The chemiluminescence may be detected by an optical procedure such as a cooled CCD camera or a photomultiplier to measure the target substance 500 contained in the subject sample. At this time, the state of the reaction system (for example, the presence or absence of prozone phenomenon) may be evaluated by comparing the amount of luminescence in the first measuring section 244 and the amount of luminescence in the second measuring section 254. The concentration (amount) of the target substance 500 in the subject sample may be measured by applying the amount of luminescence in the first measuring section 244 to a previously prepared calibration curve.

As illustrated above, the assay kit according to the present embodiment has a capturing antibody immobilized in advance in the first measuring section and the second measuring section, and captures the immune complex in the first measuring section and the second measuring section. According to the present embodiment, the same effect as the first embodiment may be obtained.

By the way, in the first embodiment and the second embodiment, an aspect in which the first measuring section and the second measuring section are provided is shown, but the number of the measuring section is not limited to this, and may be one or three or more.

Furthermore, in the second embodiment the capturing antibody immobilized in the second measuring section is an antibody binding to the target substance, but the capturing antibody immobilized in the second measuring section may be an antibody binding to an enzyme-labeled antibody. In this case, when chemiluminescence is generated on the first measuring section, it shows that the target substance is contained in the subject sample. However, when chemiluminescence is generated on the first measuring section, and yet chemiluminescence is not generated on the second measuring section, it is possible that the reaction system may not function normally. Furthermore, when chemiluminescence is not generated on the first measuring section, it shows that the target substance is not contained in the subject sample. However, it should not be judged that the target substance is not contained in the subject sample, since the reaction system may not function normally when chemiluminescence is not generated not only on the first measuring section but also on the second measuring section.

The Third Embodiment

In the first embodiment and the second embodiment, an example was shown in which one kind of the target substance was measured with one test device. In the third embodiment, an example is shown in which multiple kinds of the target substance are measured in one sampling using multiple kinds of test devices at the same time.

Figure 5:
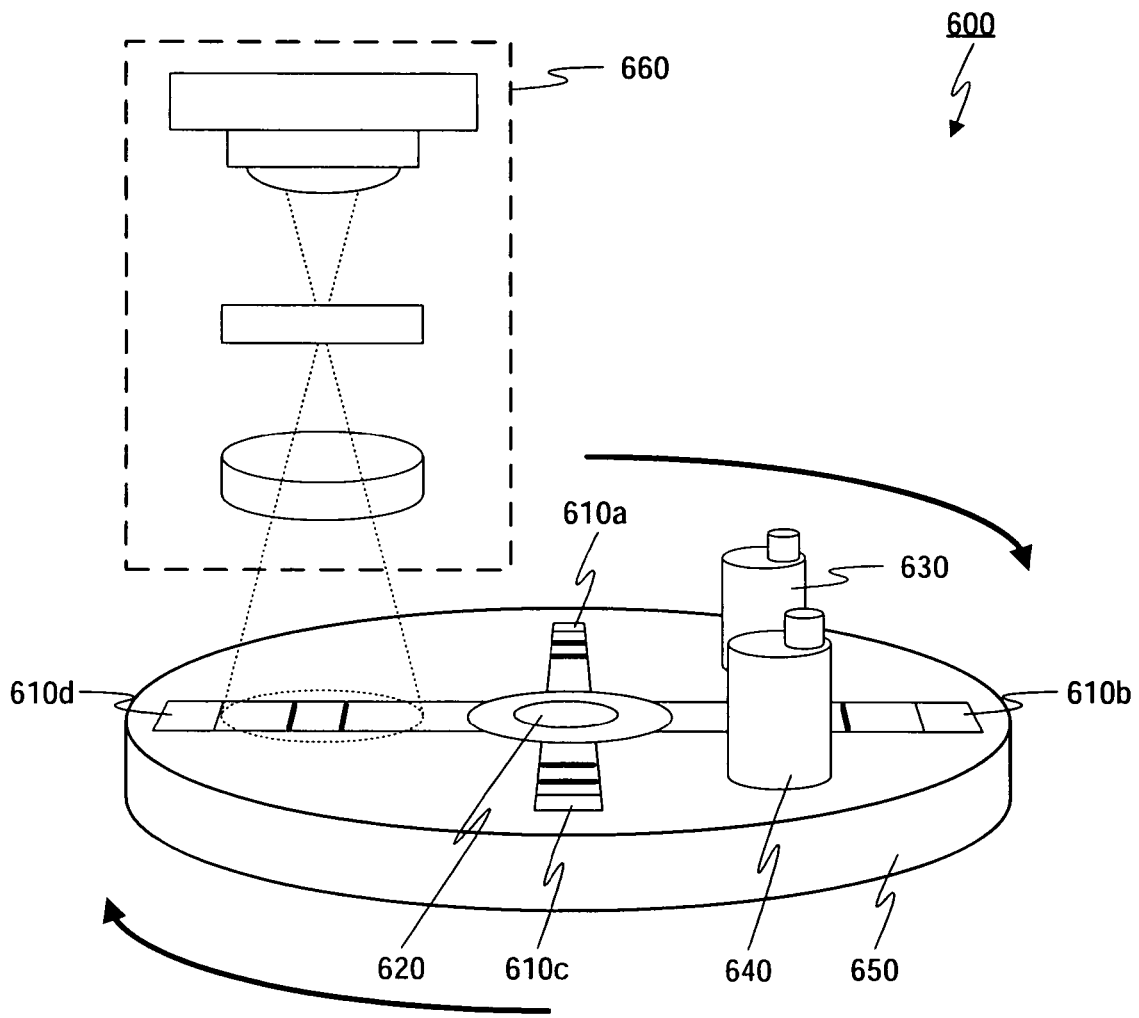
FIG. 5 is a view showing an example of the measuring equipment executing a multi-item simultaneous measurement by non-liquid phase type chemiluminescent enzyme immunoassay method of the present invention.

FIG. 5 is a schematic view showing the construction of the measuring equipment according to the third embodiment of the present invention.

In FIG. 5, the measuring equipment 600 has multiple test devices 610a to 610d, a central sample applying section 620, a storing section for a support membrane for chemiluminescent enhancer 630, a storing section for a support membrane for chemiluminescent substrate 640, a support table 650 and a detecting section 660.

The test devices 610a to 610d are same as those according to the first embodiment and the second embodiment. Each test device corresponds to a different test item respectively, and measures a different target substance respectively. For example, by arranging that the test device 610a corresponds to myoglobin, the test device 610b corresponds to troponin T, the test device 610c corresponds to troponin I, and the test device 610d corresponds to CK-MB, four items that are called markers for myocardial infarction are measured at once using only one sampling in a small amount. Therefore, pathological analyses of myocardial infarction are executed faster, and it is necessary for the selection of treatment method and judgment of convalescence.

The central sample applying section 620 is a section to be applied with a subject sample, and is constructed of, for example, nonwoven fabric made of rayon, filter paper, cotton cloth (absorbent cotton), and the like. The central sample applying section 620 is a common sample applying section for each test device 610a to 610d.

The storing section for a support membrane for chemiluminescent enhancer 630 is a vessel which stores the support membrane for chemiluminescent enhancer to overlay on each test device 610a to 610d.

The storing section for a support membrane for chemiluminescent substrate 640 is a vessel which stores the support membrane for chemiluminescent substrate to overlay on each test device 610a to 610d.

The support table 650 is a disk-shaped member to place radially each test device 610a to 610d on the same plane. The support table 650 is provided rotatably.

The detecting section 660 detects the amount of chemiluminescence generated on each test device 610a to 610d. The detecting section 660 is, for example, a cooled CCD camera.

Next, motions measuring multiple kinds of the target substances from one subject sample in the above-described measuring equipment are illustrated.

Each test device 610a to 610d is placed on the support table 650 and the subject sample is applied to the central sample applying section 620, so that an immune complex is formed on each test device 610a to 610d, and the formed immune complex is captured in the first measuring section and the second measuring section. After overlaying a support membrane for chemiluminescent enhancer and a support membrane for chemiluminescent substrate on each test device 610a to 610d by the storing section for a support membrane for chemiluminescent enhancer 630 and the storing section for a support membrane for chemiluminescent substrate 640, the detecting section 660 detects the amount of luminescence from each test device 610a to 610d serially with rotating the support table 650. The detection results are printed out from an output section (not shown). At this time, the output section may print out not the detection results of the amount of luminescence but the concentration of each target substance calculated from the detection results.

As illustrated above, in the measuring equipment according to the third embodiment, multiple kinds of the target substances are measured with multiple kinds of test devices. According to the present embodiment, multiple items are measured simultaneously in one sampling, in addition to the effect according to the first embodiment. For example, according to the present embodiment, 5 to 10 items can be measured simultaneously with 50 µL subject sample.

The followings further illustrate the present invention with reference to Examples. In addition, the scope of the present invention is not construed as limited by Examples.

EXAMPLE 1

Example 1 shows an example in which prostate-specific antigen (hereafter abbreviated as "PSA") is measured with the assay kit according to the first embodiment.

(1) Assay Kit

In the present Example, nitrocellulose membrane (25 mm long×5 mm wide×0.2 mm thick) as a support base, filter paper (20 mm long×5 mm wide×1 mm thick) as a sample applying section, glass fiber (7 mm long×5 mm wide×0.8 mm thick) as a labeled-antibody holding section, and filter paper (18 mm long×5 mm wide×1 mm thick) as an absorption section were used. The sample applying section and the labeled-antibody holding section were brought into contact with each other, and the distance between the labeled-antibody holding section and the first measuring section was set 6 mm, the distance between the first measuring section and the second measuring section was set 4 mm, and the distance between the second measuring section and the absorption section was set 8 mm. Streptavidin (Wako Pure Chemical Industries, Ltd) was immobilized on the first measuring section and the second measuring section. ALP-labeled anti-human PSA mouse monoclonal antibody (Shibayagi) was used as an enzyme-labeled antibody, and biotin-labeled anti-human PSA mouse monoclonal antibody (in-house product) was used as an antibody labeled with a substance binding to a measuring section. A cellulose acetate membrane (2 mm long×7 mm wide×0.1 mm thick) immersed with CDP-Star (0.25 mM: Roche Diagnostics) as a support membrane for chemiluminescent substrate was used, and a cellulose acetate membrane (1.5 mm long×7 mm wide×0.1 mm thick) immersed with Nitro-Block II (10% (v/v): Tropix) as a support membrane for chemiluminescent enhancer was used.

(2) Subject Samples

In the present Example, PSA was measured as a subject. Dilution series (0, 0.001, 0.100 ng/mL) of PSA (International Immunology Corporation (IIC)) was prepared with PBS and used as a subject sample.

(3) Measurement

The subject samples (20 µL) of each concentration prepared in (2) were added dropwise in sample applying sections of each different test device, respectively. 5 minutes after the dropwise addition, a support membrane for chemiluminescent enhancer was overlaid on the first measuring section and the second measuring section of each test device, on which a support membrane for chemiluminescent substrate was further overlaid. After that, cooled CCD camera (Hamamatsu Photonics K.K.: C4742-95) was used to measure the amount of luminescence in the first measuring section and the second measuring section every 10 seconds for 2 hours.

(4) Results

Figure 6:
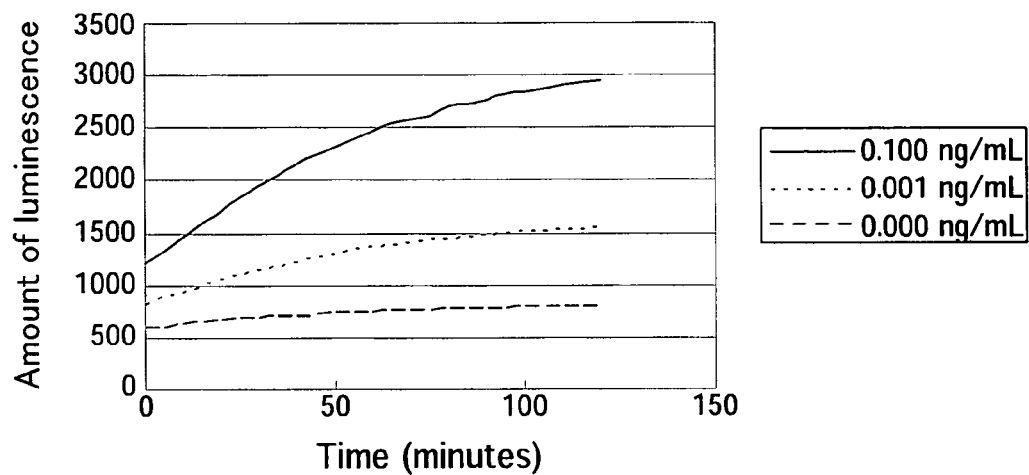
FIG. 6 is a graph showing the result of Example 1.

FIG. 6 is a graph showing the changes of the amount of luminescence measured over time. When the concentration of PSA is 0 ng/mL, the change of the amount of luminescence was hardly observed. On the other hand, when PSA was present (0.001, 0.100 ng/mL), the amount of luminescence was increased with the course of time, and after some time, the amount was saturated and reached to a steady level. Furthermore, it was observed that the higher the concentration of PSA is, the stronger the amount of luminescence becomes. Based on these results, the ratio of change of the amount of luminescence in a given time is calculated, and a calibration curve showing the relation between the concentration of PSA and the amount of luminescence can be prepared. Thus, it is found that a target substance can be measured with a small amount of subject sample in high sensitivity (0.001 ng/mL or less) in the chemiluminescent enzyme immunoassay method of the present invention.

EXAMPLE 2

In Example 2, an example is shown in which alpha-feto-protein (hereafter abbreviated as "AFP"), a marker for hepatic carcinoma, was measured with the assay kit according to the second embodiment.

(1) Assay Kit

In the present example, nitrocellulose membrane (25 mm long×5 mm wide×0.2 mm thick) as a support base, filter paper (20 mm long×5 mm wide×1 mm thick) as a sample applying section, glass fiber (7 mm long×5 mm wide×0.8 mm thick) as a labeled-antibody holding section, and filter paper (18 mm long×5 mm wide×1 mm thick) as an absorption section were used. The sample applying section and the labeled-antibody holding section were brought into contact with each other, the distance between the labeled-antibody holding section and the first measuring section was set 6 mm, the distance between the first measuring section and the second measuring section was set 4 mm, and the distance between the second measuring section and the absorption section was set 8 mm. Anti-human AFP mouse monoclonal antibody (IIC) was immobilized in the first measuring section and the second measuring section. ALP-labeled anti-human AFP mouse monoclonal antibody (Shibayagi) was used as an enzyme-labeled antibody. A cellulose acetate membrane (2 mm long×7 mm wide×0.1 mm thick) immersed with CDP-Star (0.25 mM: Roche Diagnostics) as a support membrane for chemiluminescent substrate was used, and a cellulose acetate membrane (1.5 mm long×7 mm wide×0.1 mm thick) immersed with Nitro-Block II (10% (v/v): Tropix) as a support membrane for chemiluminescent enhancer was used.

(2) Subject Samples

In the present example, AFP was measured as a subject. Dilution series (0, 0.010, 0.100, 1.000 ng/mL) of AFP (IIC) was prepared with PBS and used as a subject sample.

(3) Measurement

The subject samples (20 μL) of each concentration prepared in (2) were added dropwise in sample applying sections of each different test device respectively. 5 minutes after the dropwise addition, a support membrane for chemiluminescent enhancer was overlaid on the first measuring section and the second measuring section of each test device, on which a support membrane for chemiluminescent substrate was further overlaid. After that, cooled CCD camera (Hamamatsu Photonics K.K.: C4742-95) was used to measure the amount of luminescence in the first measuring section and the second measuring section every 10 seconds for 2 hours.

(4) Results

Figure 7:
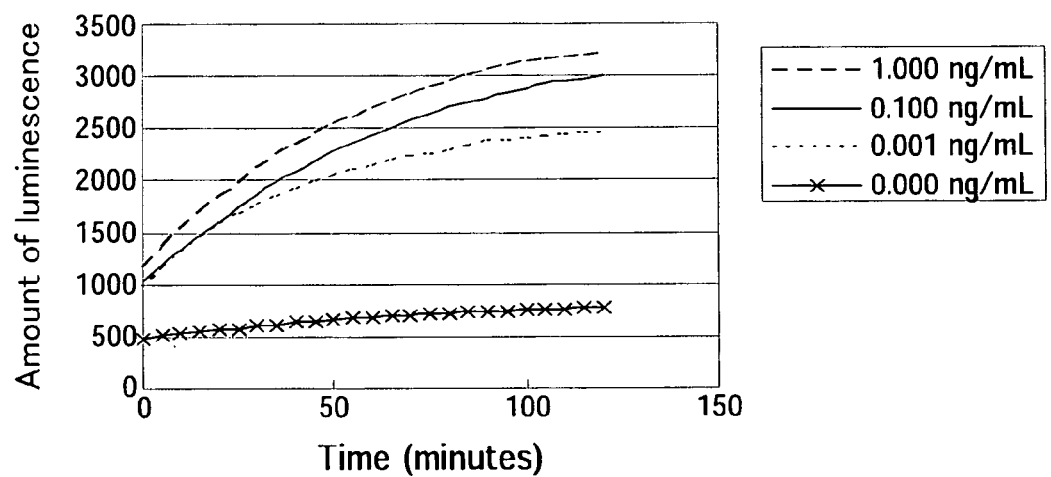
FIG. 7 is a graph showing the result of Example 2.

FIG. 7 is a graph showing the changes in the amount of luminescence measured over time. When the concentration of AFP is 0 ng/mL, the change in the amount of luminescence was hardly observed. On the other hand, when AFP was present (0.010 to 1.000 ng/mL), the amount of luminescence was increased with the course of time, and after some time, the amount was saturated and reached to a steady level. Furthermore, it was observed that the higher the concentration of AFP is, the stronger the amount of luminescence becomes. Based on these results, the ratio of change of the amount of luminescence in a given time is calculated, and a calibration curve showing the relation between the concentration of AFP and the amount of luminescence may be prepared. Thus, it is found that a target substance may be measured with a small amount of subject sample in high sensitivity (0.010 ng/mL or less) in the chemiluminescent enzyme immunoassay method of the present invention.

The present application claims the priority based on Japanese Patent Application No. 2005-342785 filed on Oct. 31, 2005. The contents described in the description of said application are herein incorporated in its entirety.

INDUSTRIAL APPLICABILITY

The chemiluminescent enzyme immunoassay method of the present invention is useful as a bed-side assay method with small number of reagent-dispensing times and small size, because a high sensitive chemiluminescent enzyme immunoassay method is performed by using a convenient non-liquid phase type reaction system. Furthermore, the assay kit of the present invention has a 100 to 1000 times higher sensitivity compared with that of conventionally-used immunochromatography methods, and test devices may be produced in an extremely compact size and the used amounts of antibodies and chemiluminescent substrates may be reduced. In addition, in view of high sensitive measurement, samples (antigens) for use can be diluted previously to use, and thus, even when the amount of blood collected from a patient is for example 10 μL, several items may be simultaneously measured by diluting the amount 10 times. Furthermore, since troublesome procedures are not required, the chemiluminescent enzyme immunoassay method of the present invention may be applied to a small-size and low-cost measuring equipment.

The invention claimed is:

1. A non-liquid phase type chemiluminescent enzyme immunoassay method, comprising the steps of:
    applying a sample solution containing a target substance to a support base having a labeled-antibody holding section containing an enzyme-labeled antibody labeled with an enzyme acting on a chemiluminescent substrate to form an immune complex containing the enzyme-labeled antibody and the target substance;
    laterally developing the sample solution including the immune complex across a surface of the support base to capture the immune complex on the support base;
    overlaying a support membrane containing the chemiluminescent substrate on the immune complex captured on the support base;
    producing a reaction product generating chemiluminescence on the support membrane by reacting the enzyme of the immune complex captured on the support base and the chemiluminescent substrate; and
    measuring an amount of the target substance by detecting an amount of luminescence generated from the reaction product positioned on the support membrane.

2. The non-liquid phase type chemiluminescent enzyme immunoassay method according to claim 1, wherein the support membrane is transparent or semitransparent.

3. The non-liquid phase type chemiluminescent enzyme immunoassay method according to claim 2, wherein the support membrane is agarose gel, polyacrylamide gel or cellulose acetate membrane.

4. The non-liquid phase type chemiluminescent enzyme immunoassay method according to claim 1, wherein the support membrane further contains a chemiluminescent enhancer.

5. The non-liquid phase type chemiluminescent enzyme immunoassay method according to claim 1, further comprising the step of overlaying a support membrane containing a chemiluminescent enhancer on the immune complex.

6. The non-liquid phase type chemiluminescent enzyme immunoassay method according to claim 5, wherein the support membrane containing the chemiluminescent enhancer is placed between the immune complex and the support membrane containing the chemiluminescent substrate.

7. The non-liquid phase type chemiluminescent enzyme immunoassay method according to claim 1, wherein the target substance contains a protein or a chemical.

8. The non-liquid phase type chemiluminescent enzyme immunoassay method according to claim 1, wherein the step of measuring includes the step of quantifying the concentration of the target substance from the detected amount of luminescence and a previously prepared calibration curve.

9. The non-liquid phase type chemiluminescent enzyme immunoassay method according to claim 1, wherein the support membrane is prepared independently of the support base.

10. An assay kit using a non-liquid phase type chemiluminescent enzyme immunoassay method, comprising
    a test device having a sample-applying section to be applied with a sample containing a target substance, a labeled-antibody holding section containing an enzyme-labeled antibody labeled with an enzyme acting on a chemiluminescent substrate, a measuring section capturing an immune complex containing the target substance and the enzyme-labeled antibody, an absorption section absorbing a liquid contained in the sample, and a support base to be placed with the sample-applying section, the labeled-antibody holding section, the measuring section and the absorption section; and
    a support membrane containing the chemiluminescent substrate and prepared so that the support membrane can be overlaid on the measuring section.

11. The assay kit according to claim 10, wherein the test device further has a second measuring section capturing the enzyme-labeled antibody or the immune complex on the support base.

12. The assay kit according to claim 10, wherein the support membrane is agarose gel, polyacrylamide gel or cellulose acetate membrane.

13. The assay kit according to claim 10, wherein the support membrane further contains a chemiluminescent enhancer.

14. The assay kit according to claim 10, wherein the kit further has a support membrane containing a chemiluminescent enhancer.

* * * * *